(12) United States Patent
Angros

(10) Patent No.: US 8,993,235 B2
(45) Date of Patent: *Mar. 31, 2015

(54) ENCAPSULATED REAGENTS AND METHODS OF USE

(71) Applicant: Lee H. Angros, Bethany, OK (US)

(72) Inventor: Lee H. Angros, Bethany, OK (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/336,500

(22) Filed: Jul. 21, 2014

(65) Prior Publication Data

US 2014/0335518 A1   Nov. 13, 2014

Related U.S. Application Data

(63) Continuation of application No. 13/944,619, filed on Jul. 17, 2013, now Pat. No. 8,785,124, which is a continuation of application No. 13/144,854, filed as application No. PCT/US2010/021200 on Jan. 15, 2010, now abandoned.

(60) Provisional application No. 61/145,269, filed on Jan. 16, 2009.

(51) Int. Cl.
| | | |
|---|---|---|
| C12Q 1/68 | (2006.01) | |
| B01L 3/00 | (2006.01) | |
| G01N 35/10 | (2006.01) | |
| G01N 35/00 | (2006.01) | |

(52) U.S. Cl.
CPC .................. *C12Q 1/6841* (2013.01); *B01L 3/52* (2013.01); *B01L 3/523* (2013.01); *C12Q 1/68* (2013.01); *B01L 2200/0673* (2013.01); *B01L 2300/18* (2013.01); *B01L 2300/1861* (2013.01); *G01N 35/1002* (2013.01); *G01N 2035/00237* (2013.01); *Y10S 435/962* (2013.01); *Y10S 435/969* (2013.01)

USPC ............ 435/6.1; 435/7.92; 435/30; 435/962; 435/969; 436/518; 436/535

(58) Field of Classification Search
None
See application file for complete search history.

(56) References Cited

U.S. PATENT DOCUMENTS

| | | | | |
|---|---|---|---|---|
| 4,241,046 | A | * | 12/1980 | Papahadjopoulos et al. . 424/420 |
| 4,372,745 | A | * | 2/1983 | Mandle et al. ................ 436/537 |
| 4,801,459 | A | * | 1/1989 | Liburdy .......................... 604/20 |
| 4,810,630 | A | * | 3/1989 | Craig et al. ................... 435/7.36 |
| 4,921,757 | A | * | 5/1990 | Wheatley et al. ........... 428/402.2 |
| 4,929,411 | A | * | 5/1990 | Usami et al. .................. 503/213 |
| 5,786,151 | A | * | 7/1998 | Sanders ...................... 435/6.12 |
| 8,029,985 | B2 | * | 10/2011 | Kriksunov et al. .......... 435/6.11 |
| 8,785,124 | B2 | * | 7/2014 | Angros .......................... 435/6.1 |
| 2003/0203040 | A1 | * | 10/2003 | Cleland et al. ............... 424/490 |
| 2006/0165746 | A1 | * | 7/2006 | Markus et al. ................ 424/405 |

FOREIGN PATENT DOCUMENTS

EP          0278116       * 12/1987 ........... G01N 33/546

OTHER PUBLICATIONS

International Search Report and Written Opinion (PCT/US/2010/021200); Feb. 23, 2010.

* cited by examiner

*Primary Examiner* — Gary W Counts
(74) *Attorney, Agent, or Firm* — Dunlap Codding, P.C.

(57) ABSTRACT

The present invention contemplates use of encapsulated aqueous and non-aqueous reagents, solutions and solvents and their use in laboratory procedures. These encapsulated aqueous or non-aqueous reagents, solutions and solvents can be completely contained or encapsulated in microcapsules or nanocapsules that can be added to an aqueous or non-aqueous carrier solution or liquid required for medical and research laboratory testing of biological or non-biological specimens.

7 Claims, No Drawings

ENCAPSULATED REAGENTS AND METHODS OF USE

CROSS REFERENCE TO RELATED APPLICATIONS

This application is a continuation of U.S. application Ser. No. 13/944,619, filed Jul. 17, 2013, now U.S. Pat. No. 8,785,124, which is a continuation of U.S. Ser. No. 13/144,854, filed Jul. 15, 2011, now abandoned, which claims priority from 35 U.S.C. 371 of International Application PCT/US2010/021200, filed Jan. 15, 2010, which claims the benefit of U.S. Provisional Application Ser. No. 61/145,269, filed Jan. 16, 2009. The entire contents of each are hereby expressly incorporated herein by reference.

STATEMENT REGARDING FEDERALLY SPONSORED RESEARCH OR DEVELOPMENT

Not applicable.

BACKGROUND OF THE INVENTION

In a microscope slide treatment method known in the prior art, a test specimen which is attached to a microscope slide is treated using two phase-separating liquids. In this method, first, an aqueous reagent is placed on an upper surface of the microscope slide to which the specimen is attached. Then a layer of mineral oil or other immiscible oil is placed over the aqueous reagent. The two different phases remain separated even after stirring or agitation. This is desired in this example, however, because the purpose of the placement of the oil layer over the aqueous reagent is to reduce the evaporation of the aqueous reagent during the timed incubation steps (e.g., heating). However, this method requires two separate steps to dispose the reagent and oil on the slide. For example, in one alternative, the aqueous reagent is placed over the biological specimen first and then, in a second step, the oil layer is placed over the aqueous reagent. Alternatively, one could envision first placing the oil layer over the biological specimen, and then placing the aqueous reagent onto the oil layer thereby wherein the aqueous reagent then submerges through the oil layer to the microscope slide surface whereby the oil layer floats on top of the aqueous reagent. A significant disadvantage of this method is that the aqueous layer tends to remain localized at the specific location where the aqueous reagent was first placed on the slide, once the oil layer is placed thereon. If the aqueous reagent is placed on top of the oil layer so the aqueous reagent layer passes through the oil layer but the aqueous reagent layer partially or entirely misses the specimen by not covering the whole specimen area, the aqueous reagent layer is fixed in that exact position once it passes through the oil layer and thus the specimen is not treated with the aqueous reagent. If one were to place, for example, a stir stick or stir device through the oil layer and down to the aqueous layer to mix or move the aqueous layer, the aqueous reagent tends to remain in its original location of placement and cannot be moved to a more useful or appropriate area upon or around the slide or specimen. This reduces the ability of the specimen to react with the reagent in this method. A solution to this problem to increase the efficiency of the process and to minimize the chances of damaging the specimen is desirable.

DETAILED DESCRIPTION OF THE INVENTION

The present invention contemplates use of encapsulated aqueous and non-aqueous reagents, solutions and solvents and their use in laboratory procedures. These encapsulated aqueous or non-aqueous reagents, solutions and solvents can be completely contained or encapsulated in microcapsules or nanocapsules that can be added to an aqueous or non-aqueous carrier solution or liquid required for medical and research laboratory testing of biological or non-biological specimens (also referred to herein as "testing" or "test" specimens). Where used herein the term "encapsulated reagent" is intended to refer also to "microencapsulated reagents" and/or to "nanoencapsulated reagents". Further, where used herein, the term "capsule" is intended to refer to "microcapsules" or "nanocapsules".

Where used herein the term "biological specimen" includes, but is not limited to, unprocessed specimens, processed specimens, paraffin embedded tissue, whole mounts, frozen sections, cell preps, cell suspensions, touch preps, thin preps, cytospins, and other biological materials or molecules including blood, urine, cerebrospinal fluids, pleural fluids, ascites fluids, biopsy materials, fine needle aspirates, pap smears, swabbed cells or tissues, microbiological preps including bacteria, viruses, parasites, protozoans, biochemicals including, but not limited to proteins, DNA, RNA, carbohydrates, lipids, ELISA reagents and analytes, synthetic macromolecules, phospholipids, support structures of biological molecules (e.g., metals, beads, plastics, polymers, glass), or any other materials attached to a biological testing substrate for processing, examination, or observation.

The capsules of the present invention are generally considered to have diameters in the range of from less than 0.001 angstrom (0.0001 nm) to 3000 microns (3000 µm). Preferably the range is from 1 angstrom (0.1 nm) to 1000 micrometers. The range can also be from 1 nanometer to 1000 microns. The shells or encapsulating material that make up the microcapsules or nanocapsules can be gelatin, polyvinyl alcohol, urea, melamine formaldehyde polymers, acrylics, urethanes, vinyl acetate copolymers, oily, lipid, or non-aqueous soluble materials and polymers, water, or aqueous based materials and polymers. The encapsulation processes used to form the encapsulated reagents include, but are not limited to, coacervation, vapor deposition, fluid bed coating, entrapment/matrix, macro-emulsion, mini-emulsion, micro-emulsion, micro-encapsulation techniques, macro-encapsulation techniques, dispersion polymerization, in situ polymerization, liposomal, alginate encapsulation, solvent phase separation, and pan coating. The micro- or nanoencapsulated reagent product can be delivered as a dry, free-flowing powder, as a slurry, or in the form of wet filter cake.

Reagents and compounds which may be microencapsulated or nanoencapsulated as contemplated for use in the present invention include, by way of example only, not by way of limitation, Dextran sulfate, formamide, SSC (sodium chloride sodium citrate solutions), DI water, Millipore™ water, RNAase-free and DNAase-free water, DAPI counter stain, propidium iodine counterstain, counterstains, salts, buffers, chemicals, DNA probes, RNA probes, protein probes, antibodies, monoclonal antibodies, polyclonal antibodies, probes, detection reagents, stains, biological stains, dyes, washes, rinses, enzymes, antigen retrieval solutions or buffers, ionic, non-ionic, anionic, cationic, neutral detergents and surfactants, thermoplastics, mountants, oils, lipids, phospholipids, molecular biological building blocks, carbohydrates, sugars, lyophilized or desiccated powder or dry reagents that can be reconstituted with and aqueous or non-aqueous solution, preservatives, cover slip media, liquefied thermoplastic cover slip medias, xylene, toluene, acetone, petroleum distillates, ferrofluids, magnetic particles in a fluid, colloidal gold conjugated reagents, iron-containing fluids, iron particles, magnetic particles, organic solvents, inorganic solvents, aqueous solvents, non-aqueous solvents, lipid based solvents, emulsions, liquid chemicals, Histology clearing reagents, Histology deparaffinizing reagents, Histology hydrating reagents, Histology dehydrating reagents, Histology fixatives, formaldehyde, alcohols, polyols, magnetic particle powders, powders, lyophilized reagents, lyophilized antibodies, lyophilized molecular probes like RNA and DNA, dry chemicals, dry, powdered, or lyophilized stains and reagents, fluorescent conjugated reagents like antibodies, stains, and molecular probes, and detection reagents, chromogens, DAB, hydrogen peroxide, naphthol phosphate, fast red chromogen, acids, bases, HCL, formic acid, glacial acetic acid, sodium hydroxide, potassium hydroxide, aqueous and non aqueous liquids, and any other reagent and/or chemicals including liquids, dry reagents, desiccated reagents, gel reagents, colloidal reagents, emulsions reagents and any other reagent or chemical known in the art of medical and research laboratory testing reagents or chemicals. These reagents will be referred to herein as "encapsulated reagents". The solutions or liquids to which these encapsulated reagents can be added may be referred to elsewhere herein as "solutions" or more particularly as "carrier solutions". The above is exemplary only and is not intended to be an exhaustive list of the reagents or compounds which may be encapsulated or used herein.

Examples contemplated herein of the use of these encapsulated reagents include for example (1) addition of aqueous-based encapsulated reagents to non-aqueous based solutions, (2) addition of non-aqueous based encapsulated reagents to aqueous-based solutions, (3) addition of aqueous-based encapsulated reagents to aqueous-based solutions, (4) addition of non-aqueous based encapsulated reagents to non-aqueous based encapsulated solutions, and (5) addition of both aqueous-based and non-aqueous based encapsulated reagents to either an aqueous- or non-aqueous solution, and wherein the resulting combination solutions contain such encapsulated reagents in a homogenous, soluble, or colloidal, emulsions, or at least partially soluble liquid mixture.

It is known that when adding a typical aqueous-based reagent to a non-aqueous solution, or vice-versa, the two different phases separate. There is therefore a need to be able to mix aqueous-based reagents with non-aqueous-based solutions, and non-aqueous-based reagents with aqueous-based solutions to form homogenous solutions of both the reagent and the solution without the usual phase separation of both. Encapsulation of the reagent as contemplated herein enables the formation of such homogenous mixtures.

The problem in the prior art method described above in the Background may be addressed by using a three-step procedure involving first disposing an aqueous detergent-containing layer over the entire area of the slide (or analytic substrate, as defined herein) where one would like the aqueous reagent layer to be positioned once the oil layer is added, or vice versa. In this method, an aqueous detergent-containing layer can be placed first on the microscope slide, followed by addition of the aqueous reagent layer, and then followed by addition of the oil layer in a third subsequent step. In the presence of these three layers, the aqueous reagent layer can be moved or mixed on the slide anywhere the aqueous detergent layer is present. However, this method is highly inefficient in both time, materials, and cost required to perform a staining protocol which requires an oil layer or liquid phase/separation protocol. A further disadvantage of this three-step method is that the aqueous detergent layer must always be added first, through either the aqueous reagent layer, or the oil layer can be added next. Still, whether the oil layer is added, second or third following addition of the aqueous reagent layer, it is obvious that the method is still requires three separate steps and is a costly time and material consuming protocol.

The present invention provides a solution to the problems of the prior art method. In the present invention, one or more reagents which are encapsulated, by microencapsulation and/or nanoencapsulation, are added to aqueous or non-aqueous solutions for use as single ready-to-use solutions for laboratory testing of specimens. The physical and/or chemical makeup of the encapsulated reagents is such that the microcapsule or nanocapsule containing the reagent is soluble, at least partial soluble, or colloidal in a solution which has a different liquid phase or density than that of the encapsulated reagent. In an alternative embodiment, the encapsulated reagents have the same or similar densities or liquid phase of the solution. Further, the microcapsule or nanocapsule could have the same or similar density or the same or similar liquid phase of the solution regardless if the reagent encapsulated therein has the same or similar liquid phase or density. It is an object of the present invention to encapsulate reagents wherein the chemical and/or physical properties of the encapsulating material (the outer shell of the capsule) are like or similar to that of the solution to which the encapsulated reagent will be added thereby allowing the capsules to be soluble, at least partially soluble, or colloidal in or with the solution. The reagent, once encapsulated, therefore would be soluble, at least partially soluble, or colloidal in relation to the solution. In a preferred embodiment of the present invention, a solution comprising at least one encapsulated reagent which has a density different from the solution, is provided and applied to a specimen. In an alternative embodiment of the present invention, a solution is provided which has at least one encapsulated reagent having a density which is the same as or similar to the solution containing it, then the solution is applied to a specimen.

The analytic substrates used in the present invention may be constructed of glass, plastic, synthetic polymers, ceramics, or metals and may be of any size or shape known in the art of laboratory examination, for example including any laboratory support structure or testing structure or device used in laboratory testing or examination including, but not limited to, microscope analytic plates, analytic substrates, medical and research laboratory testing substrates, diagnostic substrates, biological testing substrates, substrates, microscope slides, test tubes, Petri dishes, micro arrays, biochips, testing plates, containers, beads, and testing strips and any other natural or synthetic substrate or device used in the art for medical, research, laboratory, and diagnostic testing, in-vitro testing and/or analysis of at least one biological specimen.

The process wherein the microcapsule or nanocapsule opens or disintegrates upon the analytic substrate to release the reagent contained therein is referred to herein as "disruption". Disruption, once started, can be immediate (i.e., "immediate release"), or can be a slow or gradual release (i.e., "controlled" or "timed" release). The type of disruption necessary for the capsule to release its contents is referred to herein as the "disruption mode". The causes or stimuli of the disruption mode can be, for example, temperature changes or differentials, high temperature (e.g., 150° C.-200° C.), medium temperature (e.g., 100° C.-150° C.), low temperature (e.g., 25° C.-100° C.), heat, mechanical disruption, e.g., by agitation, sonic disruption, magnetic disruption, electric disruption, microwave disruption, UV light, infrared light, laser light, light, other types of electromagnetic radiation or energy, pH changes, pressure differentials, high pressure, medium pressure, low pressure, pressure changes above or below atmospheric (e.g., pressures of 1 psig-5000 psig; 1-10 psig; 10-50 psig; 50-100 psig; 100-150 psig; 150-200 psig; 200-300 psig; 300-500 psig; or 500-5000 psig), vacuum, and vacuum changes, time release, time dependent, chemical reactions, chemical changes, and physical reactions, and physical changes. Various disruption modes can be combined, e.g., temperature and pressure; pH and heat; time and pressure; and pressure and time, for example.

In an alternate embodiment, the "disruption" of the microcapsule or nanocapsules contained within a carrier solution occurs upon the combination of the carrier solution with at least one other solution or compound. The carrier solution in this embodiment has at least one reagent present in a microcapsule or nanocapsule, and the second solution optionally has at least one microcapsule or nanocapsule present which encapsulates a reagent. If the second solution doesn't have any encapsulated reagent present, the chemical activity, physical activity, or reaction when combining with the second solution can initiate disruption of the microcapsule or nanocapsule in the carrier solution. The combination of at least two solutions (carrier and second solution) each having at least one reagent present in a microcapsule or nanocapsule or only one of the two solutions having encapsulated reagent present when mixed can, in alternate embodiment, now "activate" (disrupt) the microcapsule(s) or nanocapsule(s) in the combined solutions. Activation of the microcapsule or nanocapsule is intended to mean the ability for the microcapsule or nanocapsule to become unstable or disruptable only after the at least two solutions are combined, wherein if the solutions are not combined, the microcapsule or nanocapsule are stable against disruption modes when they are in their separate solutions. Only when the at least two solution are mixed together are the microcapsule or nanocapsule disruptable in this embodiment. In an alternative embodiment, there can be one or more solutions combined to "activate" any microcapsule or nanocapsule present in at least one of the solutions of the combination.

A solution of the present invention may comprise an encapsulated reagent wherein the capsule is responsive to a single type of disruption mode, e.g., a pressure or sonic sensitive encapsulation, or a single solution may comprise a plurality of encapsulated reagents each wherein each type of capsule is responsive to a different type of disruption mode. In one embodiment, for example, a solution could contain three types of encapsulated reagents, each used in one of three different steps of a test protocol. For example, the first encapsulated reagent having a capsule with a "heating" disruption mode could be released to react with the slide specimen when the slide is heated. The second and third encapsulated reagents could have capsules having disruption modes which were not activated by or affected by heat but which were activated by a pH change or pressure change, for example, or other condition described herein.

As explained herein, embodiments of the present invention include carrier solutions which comprise only a single type of solute and carrier solutions which comprise multiple (two or more) solutes. In one embodiment of the present invention, the carrier solution can be mixed with another solution or solutions absent encapsulated reagent(s) or with encapsulated reagents, wherein the mixing of the two solutions may cause disruption of a encapsulated reagent in one, both, or all of the solutions, or the mixing of the two solutions does not disrupt the encapsulated reagent(s) but rather the mixed solutions remain in association with each other as a homogenous mixture, colloidal mixture, emulsion solution, phase separated solution, suspension solution, miscible solution, or immiscible solution, which the encapsulated reagents remain in an intact encapsulated condition. A list of reagents which may be encapsulated in accordance with the present invention is provided above. This list is exemplary only and does not constitute any limitation of the possible combinations of encapsulated reagents and reagents or solutes present in the one or more carrier solutions.

In one embodiment, the microencapsulated or nanoencapsulated reagents could be manufactured by Particle Sciences, Inc. 3894 Courtney Street, Bethlehem, Pa. 18017-8920 US and/or by Microtek Laboratories, Inc. 2400 East River Road, Dayton, Ohio 45439.

In various embodiments of the invention, exemplary methods of producing the microcapsules and nanocapsules used herein and descriptions of the capsular "shells" include, but are not limited to, those disclosed in the following U.S. patents and Published patent applications, all of which are hereby expressly incorporated by reference herein in their entireties. U.S. patents include, but are not limited to, U.S. Pat. Nos. 7,588,703, 7,462,365, 7,270,851, 7,052,766, 6,989, 196, 6,932,984, 6,913,767, 6,881,482, 6,828,025, 6,777,002, 6,767,637, 6,716,450, 6,599,627, 6,555,525, 6,465,425, 6,458,118, 6,265,389, 6,214,300, 6,146,665, 6,113,935, 6,103,271, 6,080,412, 5,925,464, 5,863,862, 5,766,637, 5,650,102, 5,643,605, 5,552,149, 5,540,927, 5,508,041, 5,503,851, 5,503,781, 5,464,932, 5,418,010, 5,407,609, 5,403,578, 5,362,424, 5,277,979, 5,204,184, 5,164,126, 5,164,096, 5,160,529, 5,100,673, 5,091,122, 5,066,436, 5,051,306, 4,942,129, 4,895,725, 4,803,168, 4,766,012, 4,764,317, 4,711,783, 4,675,189, 4,673,595, 4,594,370, 4,521,352, 4,518,547, 4,508,760, 4,389,330, 4,269,729, 4,211,668, 4,193,889, and 4,123,382. U.S. Published patent applications include, but are not limited to, 2009/0311329, 2009/0253901, 2009/0214633, 2009/0202652, 2009/0104275, 2009/0098628, 2009/0047314, 2008/0234406, 2008/0138420, 2008/0102132, 2008/0031962, 2007/0077308, 2007/0027085, 2007/0009668, 2006/0237865, 2006/0188464, 2006/0127667, 2006/0093808, 2006/0071357, 2006/0051425, 2004/0228833, 2004/0065969, 2004/0032038, 2003/0138491, 2003/0062641, 2002/0160109, and 2002/0064557.

Examples of reagent (e.g., DNA, RNA, ISH, FISH) reacting with the biological specimen.

As noted above, the encapsulated reagent could be of a different phase or density than that of the solution within which the encapsulated reagent is to be disposed. For example, a non-aqueous solution, such as an oil-based solution, could comprise a soluble, partially soluble, or colloidal suspension, of one or more encapsulated aqueous reagents for performing in situ hybridization of a DNA or RNA probe to a target DNA or RNA present in a specimen on a slide or other substrate. For example, the specimen is present on a microscope slide and the slide is heated to 70°-110° C. The oil solution with its encapsulated reagents present therein is added to the microscope slide. Heating at a temperature of 72° C., for example would cause the disruption of the capsule of the encapsulated reagent, for example, and the aqueous reagents therein would thereby be released into the oil solution. The aqueous reagents quickly separate away from the oil layer and are deposited onto the microscope slide and onto specimen thereon. Wherever the oil solution is present on the microscope slide, there would now be a layer of aqueous reagents that had separated from the oil solution and had migrated to the surface of the microscope slide. Present on the surface of the microscope slide therefore, would be an aqueous reagent layer, with the oil layer of the original solution over the aqueous reagent layer. The aqueous layer could then be agitated or stirred about the slide because the encapsulated reagent preferably had present as one of the reagents therein a detergent for enhancing the dispersion and distribution of the aqueous reagents under the oil layer and upon the slide surface and specimen thereon.

In an alternative embodiment, the microscope slide, with biological specimen attached thereto, is first flooded with a wash buffer that has at least one detergent and/or surfactant present. Excess wash buffer is removed to leave only a residual layer of wash buffer on the microscope slide and biological specimen (e.g., approximately 1-100 micro liters of wash buffer remaining on the slide). An oil-based carrier solution containing the encapsulated aqueous reagent is now added to the wet slide. The capsules of encapsulated aqueous reagent are disrupted and the aqueous reagent therein is released and deposited onto the residual wash buffer. The aqueous reagent moves to the biological specimen and surrounding areas of the microscope slide. The oil layer is above the aqueous reagent. The aqueous reagent can be moved on the microscope slide and biological specimen wherever the residual wash buffer is located by agitating the aqueous reagent or moving the oil layer which in turn would move the aqueous reagent about the biological specimen and/or microscope slide.

It is contemplated in the present invention that each reagent used in an in-situ hybridization process or other treatment methods contemplated herein can be encapsulated separately, or as mixtures that are encapsulated together. The reagents necessary for a denaturing and hybridization step of the in-situ hybridization protocol can be, for example, formamide, dextran sulfate, DI water, detergents, and the required DNA or RNA probe for example. This single solution comprising reagent capsules dispersed therein can be used for the steps of denaturing and hybridization of the target nucleic acid specimen is a novel one step solution which features all the advantages of use of an oil layer to inhibit evaporation. The use of such a single solution of the present invention is novel because in the prior art process of co-denaturing a nucleic acid with heat to denature and hybridize a nucleic acid to the target DNA present in a specimen attached to a microscope slide, one would necessarily have to use a slide having a sealed cover slip sealed with an adhesive over the specimen with the nucleic probe mixture placed underneath the sealed cover slip. In the method of the prior art, after heating, usually at 72° C. for 10 minutes, for example, the attached cover slip then must be removed which can cause damage to the specimen. Alternatively, the novel method of the present invention, wherein a single solution that has all the necessary reagents for hybridization present in microcapsules or nanocapsules is used, eliminates all the multiple steps of having to add different reagents and the manual steps of preparation during an in-situ hybridization. The single solution method of the present invention has all the necessary reagents, present within capsules in the solution, so there is no waste of reagents such as of very expensive nucleic acid probes. The single solution of the present invention may be added to the specimen on the microscope slide or other biological container or substrate. During the co-denaturing step in the present invention, the heat (or other disrupting mode contemplated herein) disrupts the microcapsules or nanocapsules thereby causing release of the reagents onto the specimen. There is no need for a cover slip to cover the specimen and reagents during the hybridization process because the single solution may be oil based while the reagents encapsulated may be aqueous-based. The oil phase in the solution will separate from the aqueous phase comprising the released reagents, thereby forming an evaporation barrier over the aqueous reagents thereby inhibiting the evaporation of the aqueous reagents during the heating or denaturing of the DNA or RNA of the target specimen. This single oil-based solution containing the encapsulated aqueous reagents can be applied by a dropper bottle, pipette, or any other type of dispenser including the dispenser described below and those noted for example in U.S. published applications 2006/0281116, 2006/0275889, and 2006/0275861, each of which is expressly incorporated herein by reference.

In a preferred embodiment, the encapsulated reagent is also very stable and has a long shelf life of greater than one year at room temperature or under 2-4° C. refrigeration vs. the non-encapsulated reagent that would normally require freezer storage at −20° C. or ultra cold freezer storage below 0° C. to maintain its freshness and viability. The encapsulation protects the temperature sensitive reagent and the reagent, as encapsulated by the methods of the present invention has a very long shelf life at normal refrigeration (2-4° C.) or at room temperature (25-30° C.). This stability provided by encapsulating the temperature-sensitive reagents is advantageous during the packing and shipping of these reagents. Many of the conventional, non-encapsulated, reagents listed herein must be shipped via "Next Day Air" in a container that is cooled by cold packs or dry ice. The encapsulated temperature sensitive reagents of the present invention can instead be shipped ground in a normal shipping container which is more cost effective without sacrificing freshness or degradation due to insufficient packing, insufficient temperature controlled shipping environments, and increasingly high shipping fees of next day air shipping requirements of the non-encapsulated temperature sensitive reagents. The encapsulation of the present invention inhibits the degradation of these proteins (e.g., antibodies) and chemical from bacterial or fungal attack or degradation. The capsules preferably have anti-fungal and anti-bacterial properties to inhibit the degradation of these proteins and chemicals when stored at room temperature or at refrigerated conditions and during shipping and use.

One embodiment of the invention is directed to a novel deparaffinizing solution. In this embodiment, one or more deparaffinizing reagents such as, but not limited to, like xylene, petroleum distillates, or other non-aqueous deparaffinizing solutions and solvents have dispersed therein an encapsulated reagent such as (but not limited to) an alcohol or other water soluble substance. This deparaffinizing solution can be placed onto the paraffin embedded tissue section thereby causing the paraffin associated with the biological specimen to soften and dissolve into the deparaffinizing reagent thereby removing the paraffin from the microscope slide and the biological specimen. Following dissolution of the paraffin, the microscope slide and the biological specimen must now be rinsed with a chemical solution that is miscible with the deparaffinizing solution. In the present invention, this "rinsing" solution or reagent is contained within the capsules contained within the deparaffinizing solution. If the deparaffinizing solution was xylene for example, the encapsulated rinse agent therein could be a reagent grade alcohol, for example. This alcohol is miscible with the xylene deparaffinizing solution. The capsules would then be disrupted by exposure of xylene/paraffin mixture to a predetermined disruption condition such as described elsewhere herein causing release of the alcohol into the xylene/paraffin mixture. The alcohol/xylene/paraffin mixture would then rinsed or removed from the slide (or analytic substrate) and biological specimen by an aqueous reagent (such as, but not limited to, water) which is miscible with the alcohol/xylene/paraffin mixture. The alcohol in this one-step deparaffinizing solution is released from the microencapsules by a condition such as time, heat, pressure, vacuum, mechanical disruption or combinations thereof, or other conditions described herein. This release of the alcohol into the deparaffinizing solution makes an alcohol/xylene/paraffin liquid that can easily be rinsed by an aqueous rinse buffer. The advantage of this deparaffinizing solution which contains the encapsulated alcohol is that there are fewer steps necessary for deparaffinization and the use of minimal reagents that can be used effectively and efficiently with less waste and reduced disposal cost when dealing with hazardous deparaffinizing solutions like xylene. Although the example of deparaffinization provided above describes the use of xylene and alcohol, other deparaffinizing solutions are known and contemplated for use instead. For example, deparaffinizing solutions that are aqueous-based can be used with the above-mentioned example of the present invention. Any deparaffinizing solution, whether aqueous or non-aqueous based, can be used as long as there is at least one microencapsulated reagent present in the deparaffinizing solution that is soluble, miscible, colloidal, or at least partially soluble in the deparaffinizing solution to prepare the paraffin/deparaffinizing solution to be rinsed with an aqueous buffer. An example of an aqueous-based deparaffinizing solution is the use of detergents in water or in water and solvent compositions (i.e., polar and non-polar solvents with detergents in water). The deparaffinizing carrier solution whether aqueous based or non-aqueous based can have in the alcohol-containing capsule an additive, such as a surfactant, detergent, polyols, or other component. Or in an alternate embodiment, these additives can be encapsulated in their own microcapsules or nano-capsules. The reagents may be encapsulated by any appropriate means contemplated in any of the description, patents, or published applications described herein.

The encapsulation material used to form the microcapsules or nanocapsules of the present invention, in an alternate embodiment, can also have magnetic properties and/or electrical properties. Alternatively, the encapsulation material can be acted on by a magnetic current or electrical current present within or adjacent the solution for use with the magnets described elsewhere herein. These magnetic and/or electrical properties of the capsules may be advantageous when it becomes necessary to mix, agitate, align, or otherwise move the capsules in relation to the solution or the specimen. For example, capsules that have magnetic properties can be moved toward or away from the specimen by magnets associated with the apparatus upon which the slide is placed, such as the instruments described in the published U.S. patent applications noted above. The magnets can, for example, move certain capsules toward the specimen just before disruption of the capsules to have the reagents as close to the specimen as possible to reduce the time of incubation and efficiency of the binding activity of the reagent with the specimen. Further, in other embodiments, the capsules can have a net charge such that they can be acted on by electrical currents to be pulled toward or repelled from the specimen or solution or other location on the microscope slide. For example, an electrical current may pass through the solution thereby pulling the charged capsules toward the specimen just prior to disruption. Alternatively, the polarity of the electrical current could be reversed to move the expelled or disrupted capsules out of the way of a different capsule containing a different reagent moving toward the specimen for the next subsequent reagent step. The electrical and/or magnetic properties of the capsule have further advantages of enabling the capsules to be mobile or to move in the solution when an electrical field or magnetic field is generated about the solution for mixing the capsules, or mixing the reagent or reagents disrupted from the capsules, for example, or by moving the disrupted capsules thereby producing a swirling, moving, or agitation motion in the solution or its respective liquid phase to mix or agitate reagents in relation to the specimen. The capsules can be moved, or the remains of the disrupted capsules can be moved, by a magnetic field or electrical field or both, to agitate, move, or mobilize other non-disrupted capsules, expelled reagents, and or the solution.

In another embodiment of the present invention, the capsules may have magnetic or electrical properties present on or within each capsule in the solution which can be used to evenly distribute or dispense the capsules in the solution. Each capsule or groups of similar capsules could have a positive or negative net charge present therein to repel other capsules in the solution to enhance the distribution or dispersion of different capsules within the solution, whether or not the capsule is in a magnetic field or electrical field. The net charge is part of the physical or chemical properties of the capsule at all times when in the solution, and the net charge may be changed by the chemical nature of the solution or reagents expelled in certain embodiments. For example, a pH change in the liquid phase of the solution or the liquid phase of the reagent can change or maintain the net charge of the capsule. The capsule, once disrupted, can maintain the same net charge as prior to disruption, or can have its charge changed after disruption. This is advantageous when placing the capsule under an electrical current or magnetic current and having a subsequent different result to the effects of the current on the capsule based on the initial net charge of the capsule before disruption or after disruption.

The encapsulation material used herein to make the encapsulated reagents may comprise micro-iron particles, or may be coated with an inert plastic or polymeric material.

The micro-iron particles of the encapsulation material can be any ferro containing particle (Fe) or other metal particles that can be moved by a magnet which is known and contemplated. The particle can be of the size less than or equal to $1 \times 10^{-10}$, $1 \times 10^{-9}$, $1 \times 10^{-8}$, $1 \times 10^{-7}$, $1 \times 10^{-8}$, or $1 \times 10^{-5}$ meters.

The micro-iron particles ("micro particles") can be coated with a ceramic, plastic or polymeric coating to help in the stability of the particles in solutions. The coating can be Teflon® or other fluropolymer, for example. The micro particle can be by itself in the capsule, in the reagent diluent or attached to a reagent in the capsule. The micro particle can be soluble, or at least partially soluble, or colloidal in the diluent solution. If the micro particle is not attached to a reagent element it could be used to mix or agitate the surrounding solution. If the micro particle is attached to the capsule or reagent in the capsule it can be used for mixing, agitating, or moving the reagent. In an alternative embodiment the diluent can have present therein an electrolyte present to produce a net charge of the reagent present and to further the effectiveness of the magnet on the reagent.

Magnets that can be used in the present invention may be permanent magnets, superconducting magnets, or resistive magnets, for example. The preferred embodiment is the use of a permanent magnet that has high temperature stability for the use in high pressure and high temperature conditions which may be used during in situ hybridization. High temperature stable permanent magnets which may be used herein are described, for example, in U.S. Pat. No. 6,451,132 which is hereby expressly incorporated herein by reference in its entirety. These high temperature permanent magnets can be subjected to temperatures exceeding 700° C. The magnets used herein may have Tesla ratings of 0.00001 Tesla to 60 Tesla for example (one Tesla equals 10,000 Gauss). Preferably the Gauss rating can be 1 to 20,000 Gauss.

Other magnets may be used such as Neodymium magnets which are a type of permanent magnet that can have the ability to retain its magnetic properties even under very high temperature conditions.

Most permanent magnets lose their magnetic properties when they are exposed to high heat conditions. A type of permanent magnet contemplated for the present invention has the grade of N42SH, the "SH" grade of Neodymium permanent magnets can be used at temperatures over 150° C. Standard "N" grade permanents magnets have a maximum operating temperature of 80° C. A "SH" grade Neodymium permanent magnet with the dimensions of 2 inches long by 1 inch wide by one eighth inch has a Gauss rating of 3095 for its surface field strength. It also has a Brmax of 13,200 Gauss and a BHmax of 42 MGOe.

EXAMPLES

Example 1

Encapsulated IHC Fast Red Chromogen Reagents

Fast Red chromogen protocols can be utilized in one embodiment of the present invention. It is well known in the art of alkaline phosphatase immunohistochemistry (IHC) reactions that a final step of the protocol is to visualize the reaction by a color change at the antigen target site by the use of an activated fast red substrate/chromogen solution that reacts with the alkaline phosphatase enzyme attached to the biotinylated antibody/streptavidin alkaline phosphatase complex. In the prior art method, chromogen activation is accomplished by adding 2 milliliters of a substrate reagent solution (naphthol-phosphate in a tris buffer) and 30-50 microliters of fast red chromogen reagent solution together to form an activated chromogen. The activated chromogen (i.e., the naphthol/tris/fast red chromogen complex) is a time dependent mixture that has a lifespan of only 30 minutes, after which the chromogen solution becomes inactive and must be rinsed off the slide. It is well known in the art of fast red chromogen chemistry that fast red chromogen is not stable at room temperature, however, the fast red reagent is stable up to one year if stored under 2° C.-8° C. refrigeration. Fast red reagents can even degrade during shipment of the reagent from the manufacture to the end user. In the present invention, microencapsulated or nanoencapsulated chromagen present in a carrier solution can be used to make the "two part" fast red reagent system of the prior art into a single temperature stable solution that has both reagents present in a single solution and that is stable at room temperature and doesn't have to be refrigerated during shipping. In a particular advantageous embodiment of the present invention, the carrier solution is the naphthol-phosphate/buffer reagent, and the fast red reagent is encapsulated separately therein. When the time comes to expose the fast red chromogen to the biological specimen, the technician can add the novel single fast red/carrier solution to the biological specimen. The encapsulated reagents are disrupted by one of the methods described elsewhere herein. When the encapsulated fast red chromagen reagents are free to mix together, the fast red chromogen becomes activated and can now form a color change when it comes in contact with the alkaline phosphatase enzyme. This single solution can be any combination of the required encapsulated reagents to render the single solution stable at room temperature as well as at a refrigerated condition. One can envision there would be a multitude of combinations of encapsulated reagents, in the carrier solution, to product a stable single solution fast red chromogen reagent. In one example of the present invention, the fast red chromogen single solution comprises deionized water as the carrier solution and the remaining required reagents can be encapsulated separately or together or any combination of a single reagent type per encapsulation or any combination of reagents in the same encapsulation which can be disrupted to form an activate fast red chromogen reagent which would be activated and ready for use. In another embodiment, the deionized can have the tris buffer and naphthol present in its solution, and only the fast red chromogen reagent is encapsulated. In a preferred embodiment, the carrier solution is comprised of deionized water, naphthol phosphate, and Tris buffer. The fast red chromogen reagent comprises a desiccated, lyophilized, dry, or powdered state and encapsulated. This solution is very stable at room temperatures, refrigerated temperatures, and shipping temperatures. In one example of its use, this fast red chromogen-encapsulated solution is placed onto the biological specimen and the solution is subject to a pressurized environment (e.g., 0.01 psig to 5000 psig, preferably 1-200 psig) which disrupts the desiccated, lyophilized, dry, or powdered encapsulated fast red reagent. The fast red reagent is quickly reconstituted by the carrier solution and further reacts with the carrier solution's reagents to form an activated fast red chromogen able to react with the biological specimen's labeled antigen. This method of use can be performed using the methods and apparatuses of published U.S. patent applications 2006/0281116, 2006/0275889, and 2006/0275861, for example. Alternatively, the disruption of the capsule can also be caused by any of the disruption modes listed elsewhere in this specification. The present invention is also contemplated for use with other chromogens such as horseradish peroxidase chromogens. The chemicals in this case include hydrogen peroxide, deionized water, buffer, and DAB (3,3'-diaminobenzidine). The present invention also contemplates that any combination of two or more reagents can be encapsulated (e.g., 2, 3, 4, 5, 6, 7, 8, 9, 10, 11, 12, 13, 14, 15, 16, 17, 18, 19, 20, or more), either together (if compatible) or separately encapsulated in a carrier solution. The present invention thus contemplates there can be at least one or more reagents encapsulated and present in a carrier solution. Any number of combinations of encapsulated reagents and carrier solution reagents is contemplated. A list of reagents which can be encapsulated or present in the carrier solution is provided elsewhere herein. This list is for example only, is not exhaustive, and does not constitute any limitation of the possible combinations of encapsulated reagent and reagent present in the carrier solution.

Example 2

Encapsulated DAB Chromogen Reagents

As noted the present invention can be used with other chromogens such as horseradish peroxidase chromogens. The chemicals used in this embodiment are hydrogen peroxide, deionized water, buffer, and DAB (3,3'-diaminobenzidine), and DAB enhancers. In one example, the carrier solution comprises the buffer and hydrogen peroxide, and DAB can be the encapsulated reagent in the carrier solution. What in the prior art was a three part, non-waiting system (buffer/DAB/hydrogen peroxide) necessary to obtain an activated chromogen is now, with the present invention, a one-step, one solution DAB chromogen. In this embodiment of the present invention, the encapsulated DAB is released under disruption conditions to combine with the buffer and hydrogen peroxide to activate the DAB chromogen for use. There can be multiple encapsulated reagents that are disrupted by different disruption modes, an example of which is the last step of DAB chromogen, wherein the DAB chromogen attached to the biological specimen is "enhanced" with a copper sulfate for changing the color of DAB form brown to a darker brown or black in color. The encapsulated copper sulfate in the carrier solution can be disrupted and released into the carrier solution, at the last step of the reaction, by any of the modes listed. Now what once was a 4 part system (in the prior art method) to activate DAB and enhance its color is now a single solution of the present invention that has two chemicals (DAB and Copper sulfate) encapsulated that can be released under a different disruption modes at different times in the reaction. It is obvious that the combination of carrier solution and encapsulated reagent can be changed. For example the buffer and DAB could be free in the carrier solution and the hydrogen peroxide could be the encapsulated component which is released under disruption to activate the chromogen for use.

Example 3

Encapsulated Pre-Treatment Enzymes

Any of the known enzymes that are used to digest the biological specimens such as pepsin, ficin, and proteases can be encapsulated for use as contemplated in the present invention. These proteins can be unstable in storage and during conventional use. The present invention contemplates encapsulated proteins in an aqueous carrier buffered solution and wherein when the disruption of choice occurs, the enzyme is released and able to react with the biological specimen. The present invention protects the enzyme from degradation during storage. These enzymes now can be stored at room temperature if desired. The microencapsulation protects the enzyme from degradation.

Encapsulated Antibodies

Any of the known antibodies that are used to attach to biological specimens during staining and/or antigen retrieval are contemplated for use herein. Presently, these antibodies can be unstable in storage and during use. The present invention can encapsulate these proteins in an aqueous carrier buffered solution and when the disruption of choice occurs, the antibody (or antibodies) is released and able to react with the biological specimen. The present invention protects the antibody from degradation during storage. These antibodies now can be stored at room temperature if desired. The microencapsulation protects the antibodies from degradation. Antibodies of the present invention can be encapsulated separately (one type of antibody per encapsulation} or together to release several antibodies to react with the biological specimen. (Several different types of antibodies in one capsule). A further possibility is each different antibody can be encapsulated in a different capsule separate from the rest which can be disrupted by the same disruption condition or by different disruption conditions. This embodiment is advantageous when performing double stains and triple stain with antibodies reacting with a biological specimen.

In an example of a triple stain, a single solution can have three different primary antibodies present in the carrier solution. Each different type of primary antibody is encapsulated into a separate type of capsule having a different type of disruption mode. In the method of its use, the first primarily antibody is disrupted and released and reacts with the biological specimen. This first primary antibody is then reacted with a detection system (e.g., a secondary biotinylated antibody/streptavidin label/chromogen) known in the art. The second primary antibody is then released by a different disruption mode and then detected. The third primary antibody is released by a different disruption mode and then detected. The single solution can even have multiple detection chemistries present to detect the primary antibodies present in the carrier solution. Any combination of primary antibodies, detection reagents, chromogens, buffers, etc. can be encapsulated in a carrier solution in accordance with the present invention. The antibodies are protected from degeneration by being encapsulated. These primary antibodies and their corresponding detection chemicals can be stored at room temperature or can be refrigerated. The preferred embodiment is storage of these reagents at room temperature. The encapsulation inhibits the degradation of these proteins (antibodies) and chemicals from bacterial or fungal attack or physical degradation. The capsules may have anti-fungal and anti-bacterial properties to inhibit the degradation of these proteins and chemicals when stored at room temperature or at refrigerated conditions.

Preferably the encapsulated reagent(s) in the carrier solutions of the present invention are stable under storage and/or shipping conditions wherein the carrier solutions with the reagents therein are exposed to temperature levels at low, refrigerated temperatures ($<20°$ C.), room temperature ($20°$ C.-$25°$ C.), or temperatures above room temperature ($>25°$ C.). The stability of the encapsulated reagents of the present inventions as well as the decreased processing time or steps to activate or use reagents are primary advantages of the present invention. The ability to store the reagents of the present invention at room temperature is a key feature and advantage of the present invention.

In one embodiment, the encapsulated reagents and carrier solutions of the present invention are used in the reagent dispensing packs and strips disclosed in U.S. Pat. Nos. 6,534,008, 6,855,292, 7,250,301, 7,476,363, 7,622,077, 7,632,467, and Published Application numbers 2006/0281116, 2006/0275889, and 2006/0275861 and pending U.S. application Ser. No. 12/550,288 each of which is expressly incorporated herein by reference in its entirety. The advantage of the use of the reagents and solutions of the present invention is that reagent dispensing packs and reagent dispensing strips using these reagents and carrier solutions can be shipped and stored at room temperature, as noted above and can be stored at room temperature. This advantage is novel because the technicians using staining apparatuses of the prior art must move their auto stainer reagents in and out of refrigerators throughout the day to load and unload their auto stainers with required reagents. This refrigeration and heating up to room temperature of the reagents shortens the life of the reagents. Further, since these reagents of the prior art require refrigeration there is generally a need to have more than one refrigerator to store all the different reagents. The reagent dispensing packs and strips which contains the reagents and carrier solutions of the present invention can be stored at room temperature in a drawer, cabinet, or on the counter next to the auto staining instrument for example. The embodiment of the present invention makes storage of testing reagents more stable and reduces the time for preparation and use. The present invention addresses the need for room temperature storage of reagents used in medical and laboratory testing, increased stability of reagents at room temperature and refrigerated conditions, decreases in the processing time to "prepare" or "activate" reagents, and reduction of steps in the use of auto staining instruments.

As noted above, the carrier solutions described herein, which have encapsulated reagents therein, may be supplied in or with or packaged in single-use or multi-use reagent containers, packs or strips for use in microscope slide staining and antigen retrieval processes and apparatuses such as, but not limited to, those described in U.S. Pat. Nos. 6,534,008; 7,250,301; 6,855,292; 7,622,077; 7,632,461 and 7,476,362, and US Published application 2006/0275889, and Pending U.S. application Ser. No. 12/550,296, each of which is expressly incorporated herein by reference in its entirety.

The present invention is not to be limited in scope by the specific embodiments and examples described herein, since such embodiments and examples are intended as but individual illustrations of one aspect of the invention and any similar or functionally equivalent embodiments are within the scope of this invention. Indeed, various modifications of the compositions and methods of the invention in addition to those shown and described herein will become apparent to those skilled in the art form the foregoing description. Changes may be made in the construction and the operation of the various components, compositions, elements, methods, and assemblies described herein or in the steps or the sequence of steps of the methods described herein without departing from the spirit and scope of the invention as defined in the following claims.

Each of the references, patents or publications cited herein is expressly incorporated herein by reference in its entirety.

What is claimed is:

1. A method of treating a biological specimen on an analytic substrate, comprising:
    disposing a liquid mixture upon an analytic substrate having a biological specimen disposed thereon and a residual wash buffer with at least one detergent present in the buffer disposed over the biological specimen, the liquid mixture comprising an oil-based carrier solution having dispersed therein a quantity of at least one of a plurality of microcapsules and a plurality of nanocapsules encapsulating at least one of a DNA probe and a RNA probe disposed in an aqueous solution containing at least one detergent; and
    disrupting the at least one of a plurality of microcapsules and a plurality of nanocapsules to cause the release of the at least one of DNA probe and RNA probe and the aqueous solution into the oil-based carrier solution such that at least one of the DNA probe and the RNA probe and the aqueous solution separate from the oil-based carrier solution so as to become available to act on or react with the biological specimen and the residual wash buffer.

2. The method of claim 1, wherein the disrupting step comprises exposing the at least one of a plurality of microcapsules and a plurality of nanocapsules to cause the release of the at least one of DNA probe and RNA probe and the aqueous solution into the oil-based carrier solution.

3. The method of claim 1, wherein the disrupting step comprises exposing the at least one of a plurality of microcapsules and a plurality of nanocapsules to a pressure differential sufficient to cause the release of the at least one of DNA probe and RNA probe and the aqueous solution into the oil-based carrier solution.

4. The method of claim 1, wherein the disrupting step comprises mechanically disrupting the at least one of a plurality of microcapsules and a plurality of nanocapsules to cause the release of the at least one of DNA probe and RNA probe and the aqueous solution into the oil-based carrier solution.

5. The method of claim 1, wherein the disrupting step comprises exposing the at least one of a plurality of microcapsules and a plurality of nanocapsules to a light energy to cause the release of the at least one of DNA probe and RNA probe and the aqueous solution into the oil-based carrier solution.

6. The method of claim 1, wherein the disrupting step comprises exposing the at least one of a plurality of microcapsules and a plurality of nanocapsules to electromagnetic radiation to cause the release of the at least one of DNA probe and RNA probe and the aqueous solution into the oil-based carrier solution.

7. The method of claim 1, wherein the disrupting step comprises exposing the at least one of a plurality of microcapsules and a plurality of nanocapsules to a chemical reaction to cause the release of the at least one of DNA probe and RNA probe and the aqueous solution into the oil-based carrier solution.

* * * * *